United States Patent [19]

Ruzicka et al.

[11] Patent Number: 4,950,232
[45] Date of Patent: Aug. 21, 1990

[54] CEREBROSPINAL FLUID SHUNT SYSTEM

[75] Inventors: Petr Ruzicka, Millburn, N.J.; Milan Ruzicka, St. Paul, Minn.

[73] Assignee: Surelab Superior Research Laboratories, St. Paul, Minn.

[21] Appl. No.: 220,365

[22] Filed: Jul. 11, 1988

Related U.S. Application Data

[63] Continuation of Ser. No. 85,288, Aug. 11, 1987, abandoned, which is a continuation of Ser. No. 762,506, Aug. 5, 1985, abandoned.

[51] Int. Cl.⁵ ............................................. A61M 25/00
[52] U.S. Cl. .......................................... 604/43; 604/96; 604/170; 604/268; 604/282
[58] Field of Search ..................................... 604/6–8, 604/43, 45, 104–105, 170, 265, 268, 280–283

[56] References Cited

U.S. PATENT DOCUMENTS

| | | | |
|---|---|---|---|
| 871,474 | 11/1907 | Buckner | 604/265 X |
| 1,383,502 | 7/1921 | Voltee . | |
| 2,393,003 | 1/1946 | Smith | 604/170 |
| 2,460,473 | 2/1949 | Smith | 604/43 |
| 2,470,665 | 5/1949 | Stiehl | 604/268 X |
| 2,548,602 | 4/1951 | Greenburg | 604/96 X |
| 3,185,150 | 5/1965 | Sorensen | 604/163 |
| 3,421,510 | 1/1969 | Kettenbach | 128/350 |
| 3,428,046 | 2/1969 | Remer et al. | 128/349 |
| 3,438,375 | 4/1969 | Ericson | 604/98 |
| 3,492,996 | 2/1970 | Fountain | 128/350 |
| 3,516,410 | 6/1970 | Hakim | 604/268 |
| 3,598,127 | 8/1971 | Wepsic | 604/265 |
| 3,626,950 | 12/1971 | Schulte | 604/268 |
| 3,769,982 | 11/1973 | Schulte | 128/350 |
| 3,999,554 | 12/1976 | Kim et al. | 604/268 X |
| 4,248,234 | 2/1981 | Assenza et al. | 604/282 X |
| 4,382,445 | 5/1983 | Sommers | 604/8 |
| 4,465,482 | 8/1984 | Tittel | 604/280 |
| 4,501,580 | 2/1985 | Glassman | 604/43 |
| 4,547,192 | 10/1985 | Brodsky et al. | 604/282 X |
| 4,559,046 | 12/1985 | Groshong et al. | 604/170 X |

FOREIGN PATENT DOCUMENTS 2240026  3/1975  France .................................. 604/63

OTHER PUBLICATIONS

Codman and Shurtleff, Inc. nine page brochure, #90–1050, "Accu-Flow Valve System".
Cordis Neurosurgical Instruments two page brochure #149-3335-L, "For the Forming . . . Leads".
"The Cordis Integral Shunt System", 18 page brochure published by the Cordis Corporation.
Codman & Shurtleff 20 page brochure No. 90-1054, "Holter Valve System".
Holter Hausner International, Inc., "Products for Neurosurgery", multipage catalog, undated.
PS Medical 28 page brochure "CSF Flow Control Shunts", undated.
Heyer Schulte four page brochure No. 100682-1-01, Mar. 77, "MPF Ventricular Catheter".
Heyer Schultz four page brochure No. 100678-1-02, Nov. 77, "Portnoy Ventricular Catheter".

Primary Examiner—C. Fred Rosenbaum
Assistant Examiner—C. Maglione
Attorney, Agent, or Firm—James R. Haller; Gregory P. Kaihoi; Mary P. Bauman

[57] ABSTRACT

A catheter useful in draining cerebrospinal fluid from the ventricles of a brain. The catheter utilizes a series of holes arranged in a helical pattern at the forward or ventricular end portion of the catheter. Exterior grooves may be provided in the ventricular end of the catheter within which the holes are protectively sheltered from contact with surrounding ventricular tissue. The catheter, and particularly its ventricular end, may be capable of elastic elongation upon insertion of a rigid stylet within the catheter, the diameter of the ventricular end portion become reduced in response to its axial elongation to facilitate disengagement of the catheter with the surrounding ventricular tissue to permit the catheter to be withdrawn.

13 Claims, 5 Drawing Sheets

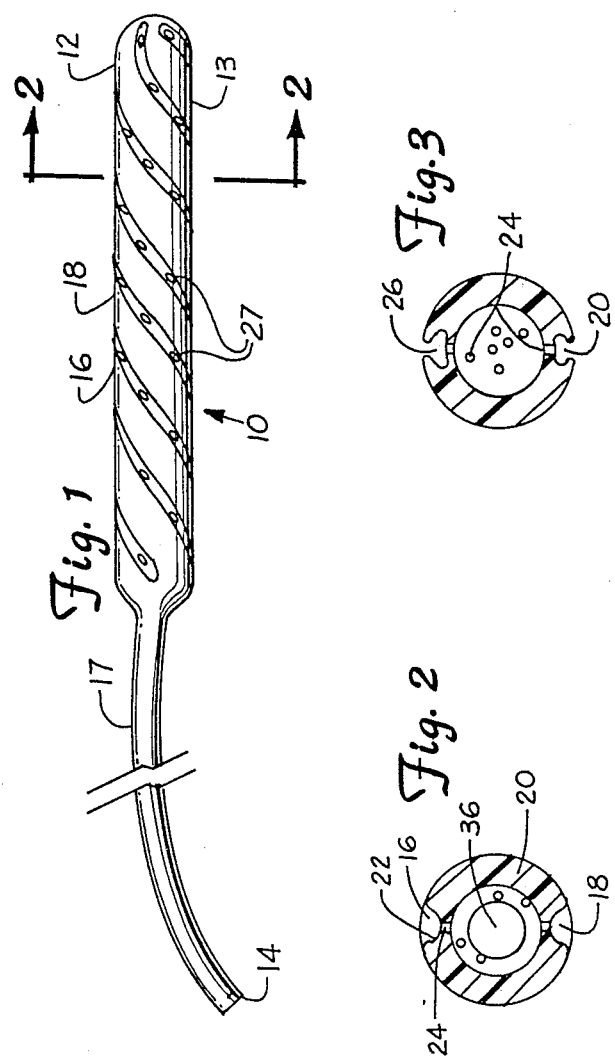

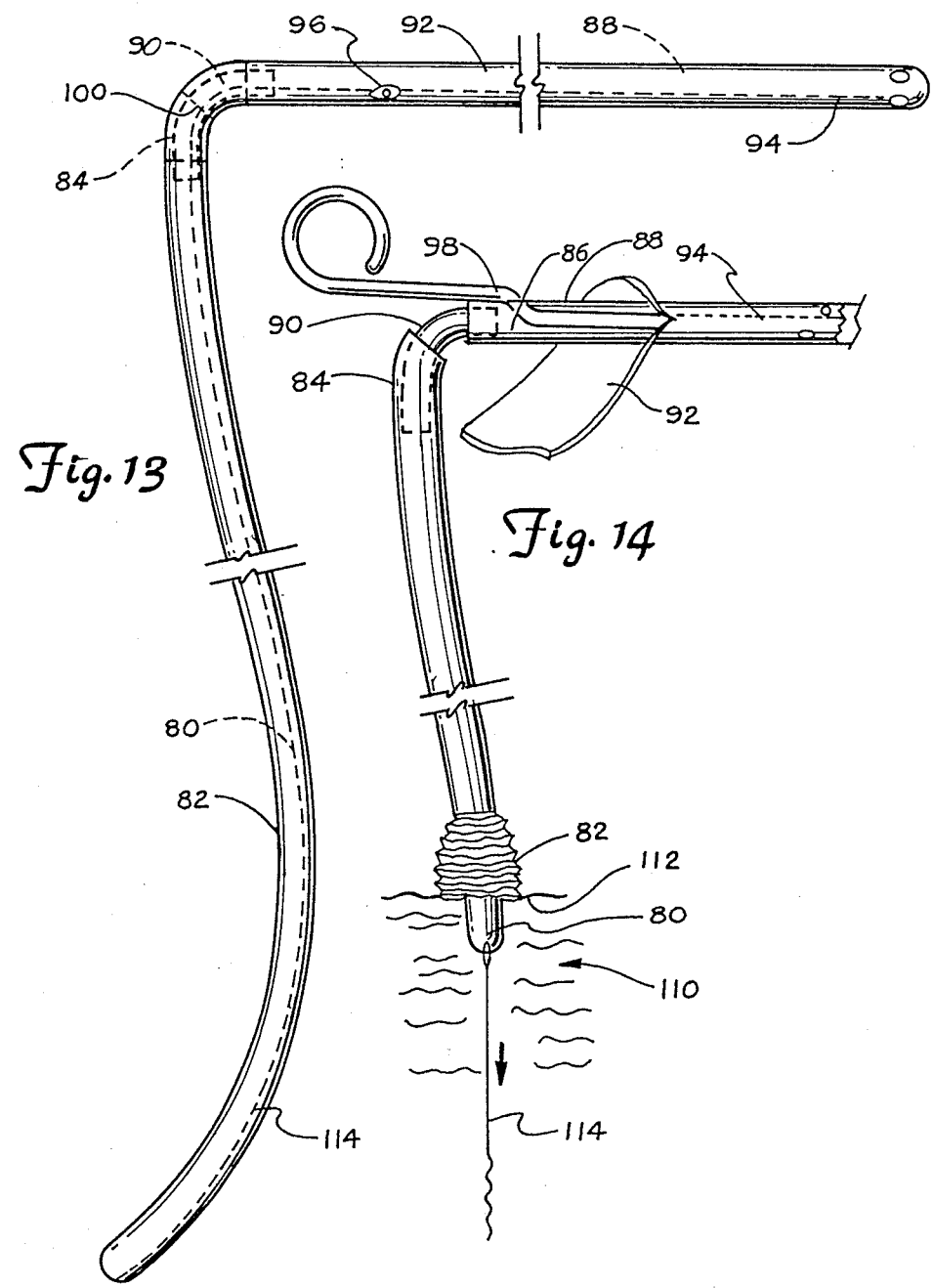

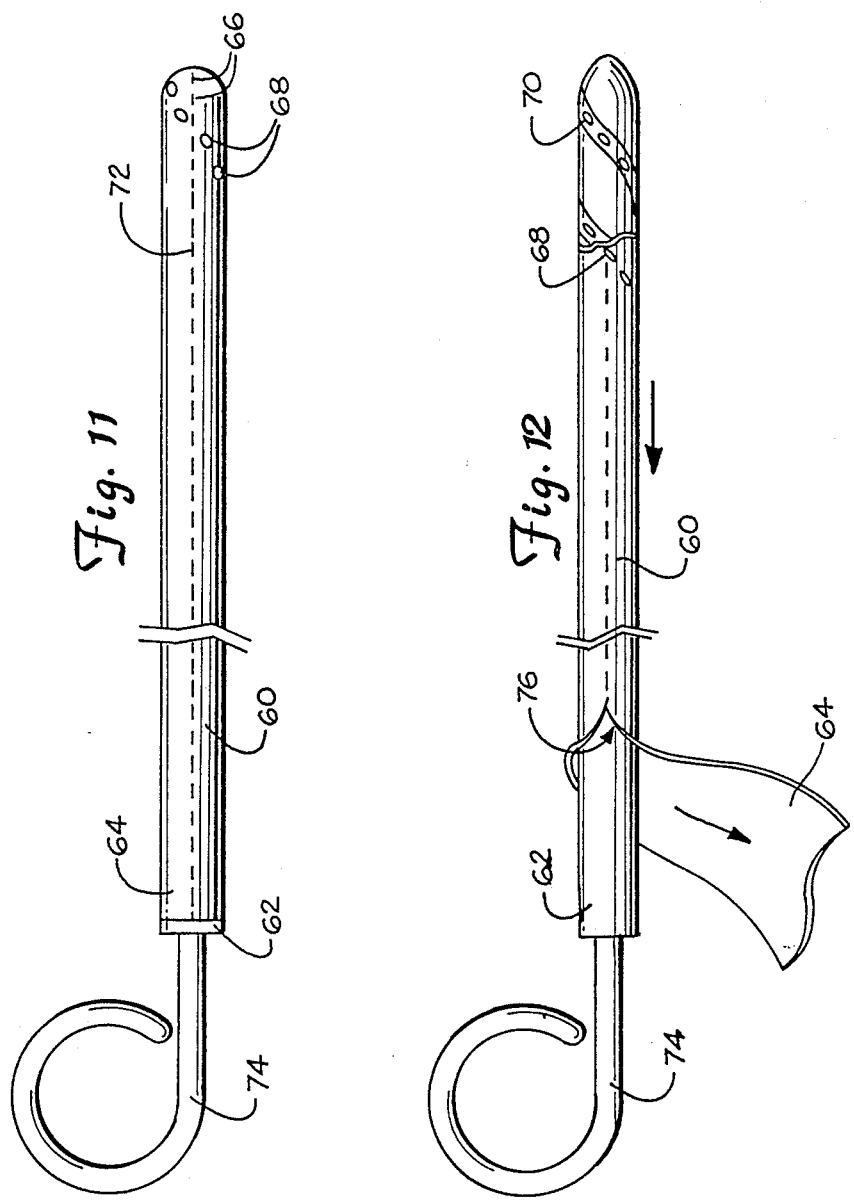

CEREBROSPINAL FLUID SHUNT SYSTEM

This application is a continuation, of application Ser. No. 762,506, filed 08/05/85 and Ser. No. 085,288 filed 08/11/87 both abandoned.

BACKGROUND OF THE INVENTION

The preferred treatment for hydrocephalus involves the use of a catheter to drain cerebrospinal fluid from ventricles of the brain. The ventricles, normally large enough to easily accommodate the end of a catheter several millimeters in diameter, have pliable walls within which is found the choroid plexus, a soft, curtain-like tissue. The end of the catheter that is received within a ventricle commonly is provided with small holes through its walls for receiving cerebrospinal fluid from the ventricle. In order to restrain the choroid plexus from coming into contact with and plugging the holes, fins or other structure, as shown in U.S. Pat. No. 3,516,410 or U.S. Pat. No. 3,626,950, has been employed, the fins extending radially outwardly from the walls of the catheter and the holes within the catheter wall being formed between adjacent fins. Continued loss of cerebrospinal fluid may lead to collapse of the ventricles, the walls of the ventricles tending to shut upon one another as cerebrospinal fluid is lost through the catheter. Such ventricular wall collapse upon an indwelling catheter tends to also block the holes in the catheter wall, preventing further drainage of cerebrospinal fluid.

Perhaps the largest health hazard in the installation of ventricular catheters is that of infection. Infection most frequently results from skin contaminants, and infection commonly becomes evident within about seven to ninety days after a ventricular catheter is surgically implanted. The catheter, as a hollow foreign object, tends to provide suitable sites for microorganism growth, and in the event of an infection, removal of the catheter system is medically indicated.

Often some tissue growth onto or into a ventricular catheter occurs (aided, it would appear, by the presence of thin-walled discs or flanges intended to physically shelter the drainage holes through the catheter wall) and this, in turn, renders removal of the catheter extremely difficult. Sometimes the catheter can be moved only very slightly in an effort to dislodge connecting tissue. From a medical standpoint, a catheter which has become bound within a ventricle by fibrous adhesions or the like should not be removed forcefully; it is thought advisable in this situation to allow the catheter to remain in place rather than risk intraventricular hemorrhage. Accordingly, a choice must often be made between risking internal hemorrhage on the one hand or persistant infection on the other.

BRIEF DESCRIPTION OF THE INVENTION

The present invention provides a ventricular catheter having a ventricular end portion adapted to be implanted in the ventricle of the brain. The ventricular end portion of the catheter in one embodiment is somewhat larger in diameter than the adjacent portion of the catheter, and is longitudinally elastic; it desirably is provided with suitable structure to bear the axial force of an inserted stylet and prevent the stylet from puncturing the end of the catheter.

The ventricular end portion of various embodiments of the catheter is provided with a plurality of drainage holes through its walls arranged in a helical pattern, and desirably one or more generally spirally or helically extending grooves are provided in the catheter walls within which the holes are protectively positioned. In this manner, the groove walls tend to shield or shelter the holes from contact with the choroid plexus and with the walls of the ventricles, thereby tending to assure fluid communication of the ventricles with the interior of the catheter from whence cerebrospinal fluid may drain. As walls of a ventricle tend to collapse upon the ventricular end portion of the catheter, the helical grooves which provide, in their troughs, a series of aligned holes, prevent the interior of the catheter from being blocked from fluid communication with the ventricle by its collapsed walls.

Further, the axial elasticity of the ventricular end of a preferred catheter embodiment enables a stylet received within the catheter to push against the sealed ventricular end and to cause the catheter to elongate, the ventricular end of the catheter thus becoming thinner in diameter and the desirably helical grooves tending to unwind, such movement of the catheter tending to gently disengage the catheter end from any encroaching choroid plexus or other fibrous ingrowth so that the catheter can be removed. In similar fashion, the catheter can readily be positioned within a ventricle by elastically elongating the ventricular end of the catheter to reduce its diameter. Once the catheter has been properly placed, withdrawal of the stylet permits the catheter to elastically regain its original diameter, which movement tends to oppose undesirable complete collapse of the ventricle, creating a "slit ventricle". This feature is particularly effective when the elastic ventricular end portion of the catheter has a "rest" diameter greater than that of the adjacent catheter portion.

Desirably, the catheter of the invention additionally is provided with a structurally supporting helical wire, for example of metal or semi-rigid plastic, the wire desirably being imbedded in the walls of the catheter and serving the function of restraining lateral collapse of the catheter. The helically configured wire does not significantly effect the axial elasticity of the catheter nor the change in diameter of the catheter's ventricular end as a function of axial elongation. The catheter may instead or additionally be provided with one or more fluid-receiving elongated bladders sized and positioned to stiffen the ventricular end portion against collapse.

DESCRIPTION OF THE DRAWINGS

FIG. 1 is a broken-away side view of a catheter of the invention;

FIG. 2 is a cross-sectional view taken along line 2—2 of FIG. 1;

FIG. 3 is a cross-sectional view similar to that of FIG. 2 but showing a slightly modified embodiment;

FIG. 11 is a broken-away view of a further embodiment of the device of the invention;

FIG. 12 is a broken-away view of the device of FIG. 11 showing a step in the use of the device;

FIG. 13 is a broken-away view of a shunt system of the invention;

FIG. 14 is a partly diagrammatic view of the shunt of FIG. 13 showing steps in the installments at the shunt system;

DESCRIPTION OF PREFERRED EMBODIMENTS

Figure 4:
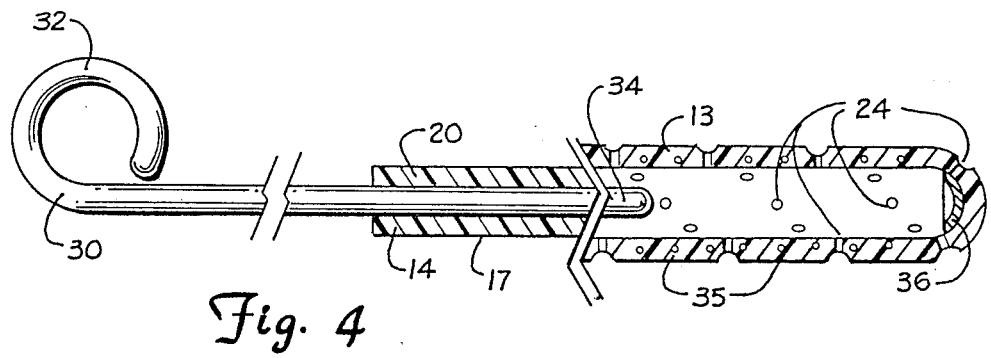
FIG. 4 is a broken-away, cross-sectional view of a catheter of the invention, with associated stylet.

Referring first to the embodiments depicted in FIGS. 1-6, the catheter of such embodiments may be made of any suitable material. An elastic surgical grade silicone rubber is preferred. The catheter, shown as (10) in the embodiment of FIG. 1, is provided with a ventricular end portion (12) and a smaller diameter drainage end portion (14), and the catheter itself is quite flexible. The drainage end (14) may be attached to other, known structure such as the valves shown in, for example, U.S. Pat. Nos. 3,601,128 and 3,827,439, the disclosures of which are incorporated herein by reference. As is known, cerebrospinal fluid is ultimately desirably drained to the right atrium of the heart or to the peritoneal cavity, but may be drained to other areas as well.

A pair of helical exterior grooves (16), (18) are formed in the outer surface of the ventricular end portion (12) of the catheter. It will be understood that FIG. 12 is a much enlarged view, and that the catheter ordinarily will not be more than several millimeters in diameter and the length of the grooved or ventricular end portion normally will not exceed about two centimeters. Typically, the outer diameter of the catheter may be on the order of 2.5-3.5 millimeters and the inner diameter may be in the range of about 1.0 to about 1.5 millimeters, the wall thickness desirably being on the order of about 0.5 millimeters. The grooves desirably extend most of the way through the thickness of the wall (20) of the catheter and desirably are substantially identical. Three or more helical grooves may be employed if desired.

Referring to FIG. 2, the walls (22) of the exterior grooves desirably rise relatively steeply from the bottom of the grooves. A series of holes (24) are formed in the grooves, the grooves and holes desirably extending, as shown in FIG. 1, substantially to the forward, closed ventricular end portion of the catheter. The walls (22) of the grooves thus arise on either side of each hole, and tend to shelter the hole from contact with the walls of a ventricle, the choroid plexus, or other tissue within the ventricle.

The embodiment of FIG. 3 is similar to that shown in FIG. 2, except that the grooves (26, (28) have been undercut somewhat so that the grooves are normally wider near the center of the catheter than at its outer surface. This embodiment tends to provide improved protection for the holes (24).

The catheter itself may be on the order of 15-20 centimeters in length, although any length may be employed. A stylet, shown as (30) in FIG. 4, comprises an elongated, relatively stiff structure such as wire, the stylet having a manually graspable end (32) and a generally smooth forward end (34) adapted to be received within the open drainage end (14) of the catheter. The end (34) desirably is smooth and rounded so as not to unduly damage the interior of the catheter, and a metal shield such as hemispherical cup (36) may be inserted in the tip end of the catheter to receive the end (34) of the stylet and to prevent the stylet from puncturing the tip of the catheter.

Figure 5:
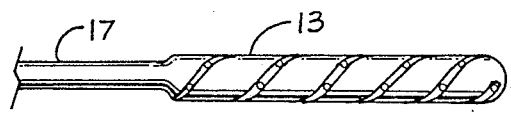
FIG. 5 is a view similar to that of FIG. 1 and showing the catheter in its axially relaxed position.
Figure 6:
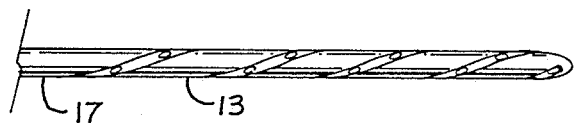
FIG. 6 is a view similar to that of FIG. 5 but showing the ventricular end of the catheter in its axially stretched position.

The ventricular end portion (12) of the catheter depicted in FIGS. 1-4 is of a diameter somewhat greater than the contiguous portion (17) of the catheter. Thus, whereas the catheter section (17) may be on the order of 2.5-3.5 millimeters in diameter, the ventricular end portion (13), which is axially elastically extensible, may have a "rest" diameter of on the order of 5 millimeters, the diameter of the ventricular end portion being so chosen that when the ventricular end portion is axially stretched by insertion of the stylet (30) (FIG. 4), the diameter of the ventricular end of the catheter can be drawn down to approximately the same diameter as the contiguous portion (17) of the catheter. This feature is shown somewhat schematically in FIGS. 5 and 6. In FIG. 5, the ventricular end portion (13) of the catheter is at rest, and has a diameter noticeably larger than that of the remainder (17) of the catheter. Once the stylet (30) is inserted into the catheter in the manner shown in FIG. 4 and the ventricular end portion of the catheter is stretched axially, a configuration not unlike that shown in FIG. 6 is attained wherein the diameter of the ventricular end portion (13) is substantially the same as that of the contiguous portion (17) of the catheter.

In use, standard surgical procedures are employed to expose the skull and to form a burr hole therein, an incision thereafter being made through the dura of sufficient size as to permit passage of the catheter. Once the position of the ventricle is established using ordinary techniques, a stylet is inserted into the catheter with the end of the stylet pushing axially upon the end of the catheter with sufficient force as to cause the catheter to elastically elongate. The catheter is advanced into the ventricle. When the catheter is properly positioned, the stylet is withdrawn, thereby permitting the ventricular end portion to elastically regain its initial shape. Using standard techniques, the catheter is to drained to areas such as the heart or abdomen.

To remove the catheter, the stylet is inserted carefully within the catheter with the end of the stylet pressing upon the end of the catheter with sufficient force as to cause the ventricular end portion of the catheter to elongate slightly. The elastic extension of the ventricular end portion of the catheter with respect to the surrounding tissue, coupled with the resulting tendency to unwind somewhat from its initial helical orientation and to undergo reduction in diameter, tends to disengage the catheter from the surrounding tissue, promoting ready removal of the catheter.

In another embodiment, the interior surface of the catheter is provided with a biologically effective antimicrobial agent to restrain the growth of microorganisms therein and thus assist in the prevention of shunt infection. Infection is perhaps the most serious complication that accompanies the use of ventricular catheters.

A biocide such as penicillin may be applied as a coating to surfaces, preferably the inner surfaces, of the catheters of the invention, as by being held in a thin polymeric film from which the biocide can readily migrate. For example, the catheter may be dipped into a solution or suspension of the biocide, or the biocide may be incorporated in the material from which the catheter is made.

Although the invention has been described with respect to the use of two or more helically oriented grooves provided in the outer surface of the ventricular end portion of the catheter, it will be understood that one groove or any practical number of grooves may be used as well. Although the angle of the grooves with respect to the axis of the catheter is not critical, it is desired that each groove traverse the complete circumference of the catheter at least once in its run from one end of the ventricular end portion of the catheter to the other.

Figure 7:
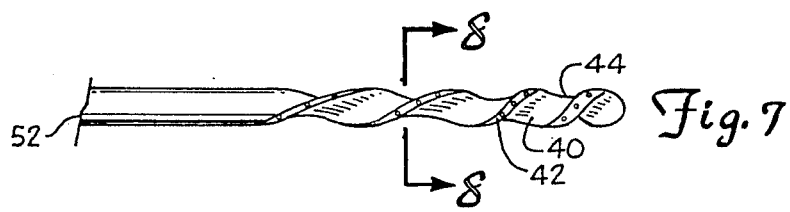
FIG. 7 is a broken-away view of a modified embodiment of a catheter of the invention.
Figure 8:
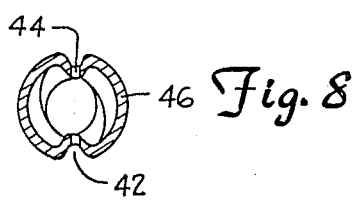
FIG. 8 is a cross-sectional view taken along line 8—8 of FIG. 7.

If desired, the ventricular end portion of the catheter of the invention may be made wholly or partially of metal, such as is shown in FIGS. 7 and 8, the forward or ventricular end portion of the catheter (40) having at least one and preferably two or more helical grooves (42) within which are positioned holes (44) extending to the interior of the catheter to drain away cerebrospinal fluid in the same manner as the catheters of FIGS. 1–6. The catheter should be of a metal which is biologically acceptable under the circumstances; catheters having platinum or gold surfaces are appropriate, as are catheters made of stainless steel. To reduce weight, the metal catheters desirably have thin walls, as shown at (46) in FIG. 8, the grooved configuration extending internally of the catheter as well, as shown in FIG. 8. Catheters made of reinforced carbon fibers which have a rigidity similar to metal produce little if any scattering effect in radiological examinations such as computeraided tomography scans or magnetic resonance imaging.

The ventricular catheter may be of rigid material throughout, or may have only the ventricular end portion — that is, the portion that enters the ventricle — made of rigid material with the remainder of the catheter being of a flexible material such as silicone rubber or a flexible metal mesh. When the catheter is entirely of a rigid material, its rigidity enables it to be appropriately positioned without use of an internal stylet. If only the ventricular end portion of the catheter is of rigid material, as is preferred, the use of a stylet for the purpose of appropriately guiding the catheter is indicated. Some flexibility is desired in the catheter to allow for shifting of brain tissue in response to physical movement of a patient.

Figure 9:
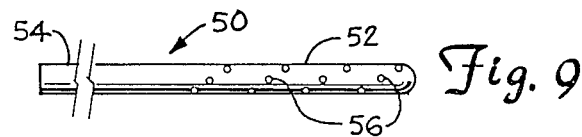
FIG. 9 is a broken away view of a modified catheter of the invention.
Figure 10:
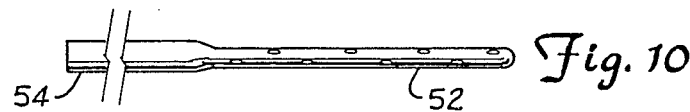
FIG. 10 is a view similar to that of FIG. 9 but showing the ventricular end of the catheter in an axially stretched position.

Referring now to FIGS. 9 and 10, a catheter (50) is provided with a forward, ventricular end portion (52) and a rearward, drainage portion (54). Drainage holes (56) are provided through the walls of the ventricular end portion (52), and are arranged in a helical pattern. In the embodiments shown in FIGS. 9 and 10, the diameters of the ventricular end and drainage portions (52) and (54) when at rest are substantially the same. When a stylet is inserted into the catheter and is pushed forwardly, the ventricular end portion (52) of the catheter extends, as shown in FIG. 10, and its diameter decreases so that it more readily may be gently disengaged from ventricular tissue and removed from a ventricle.

Although the entire length of the catheter (50) may be uniformly axially elastic, the ventricular end portion (52) of the embodiment shown in FIGS. 9 and 10 is preferably more easily elongated than is the drainage portion of that catheter, with the result that when the stylet is urged forwardly, the ventricular end portion (52) of the catheter becomes elastically elongated to a substantially greater extent than does the drainage portion (54). In this manner, when removal of a catheter from a ventricle is desired, forward pressure of a stylet within the catheter results in preferentially elongation of the ventricular end portion; that is, it is not necessary in this embodiment to cause axial elongation of the entire catheter length in order to affect axial elongation and resultant reduction in diameter of the ventricular end portion. This result can be accomplished by making the wall thickness of the ventricular end portion somewhat thinner than that of the drainage end portion or by various other means which will be evident to those skilled in the art. It will also be understood that the utilization of a ventricular end portion that is more easily axially elongated than is the drainage portion is applicable to the catheters shown in FIGS. 1 through 6 as well.

As a catheter is passed through the body of the brain during placement of the catheter end in a ventricle, liquid and solid brain matter may tend to plug or foul the drainage holes in the ventricular catheter end portion. FIGS. 11 and 12 show a modification of the catheters of the invention in which a sheath (60) is provided over at least the ventricular end portion of a catheter (62), the sheath including a rearwardly extending portion which may be grasped by a surgeon when the catheter has been properly placed. The sheath is desirably of tough but flexible material such as a polypropylene film, and is provided with a tear-open forward end formed, for example, by employing a parting line formed by a series of closely spaced and aligned small holes or slots (66). An appropriate lubricant such as sterile surgical jelly may be placed between the catheter and sheath to permit the sheath to be readily pulled rearwardly from the catheter, and one or more holes (68) may be formed in the forward or ventricular end portion of the sheath in communication with the underlying drainage holes (70) of the catheter. The parting line (72) formed by the holes or slots (66) desirably extend rearwardly to the rearward end of the sheath to aid in removal of the sheath.

In use, a stylet (72) of the type earlier described is inserted in the catheter and the catheter, with protective sheath, is advanced into the brain body until its ventricular end is appropriately positioned in a ventricle. The onset of fluid flow from the ventricle, facilitated by the aligned holes (68), (70) in the sheath and catheter, indicates proper catheter placement. While maintaining light forward hand pressure on the stylet, the surgeon then draws the sheath rearwardly, causing the sheath to open at its forward end and to slide rearwardly as shown in FIG. 12 to expose the ventricular end portion. If, as is preferred, the parting line (72) runs rearwardly to the end of the sheath, the sheath may be split (as shown at (76) in FIG. 12) as it emerges from the burr hole; alternatively the sheath may simply be gathered at the rearward end of the catheter for removal after the stylet is withdrawn.

To enable the catheters of the invention to be readily viewed by X-ray, radio-opaque materials such as metal particles may be incorporated in the catheter walls. This purpose is also served through the use of a radio-opaque metal wire helix embedded in the catheter walls.

The above-described catheters may be used with various lengths of tubing, the latter commonly being drawn beneath the skin to a desired body location such as the right atrium or the abdomen to drain cerebrospinal fluid from the catheters. FIGS. 13 and 14 show the use of catheters in a cerebrospinal fluid shunt system which in its preferred embodiment provides a catheter, a length of drainage tubing; an intermediate connector, and sterile packaging enabling introduction of the catheter and drainage tubing under conditions minimizing the chances of infection.

A drainage tube, designated (80), is provided within a protective, flexible, tubular cover (82). One end (84) of the drainage tube is connected to the adjacent end (86) of a catheter (88) by means of connector means typified in the drawing by a right-angled section of tubing (90). It will be understood that the connector means may include one or more of the devices commonly employed between a ventricular catheter and drainage tubing such as small pumps, valves opening under predetermined pressure differentials, plugs providing hypodermic needle access to the catheter and the like. Such devices are well known, and certain of them are described in Hakim, U.S. Pat. No. 3,516,410, Schulte et al, U.S. Pat. No. 3,827,439, Schulte, U.S. Pat. No. 3,769,982 and Holter et al, U.S. Pat. No. 2,969,066, the disclosures of which are incorporated herein by reference.

As earlier described, the catheter (88) may be provided with a protective, tubular sheath (92) which can be drawn rearwardly of the catheter to expose its forward, ventricular end portion. The sheath (92) may have a tear line (94) enabling the sheath to be removed from the catheter in the manner earlier described. A hole (96) may be formed along the length of the catheter through which a stylet (98) may be passed; the stylet may be straight or may be bent as shown in FIG. 14, and the stylet is inserted through the hole (96) and then is passed forwardly into contact with the tip of the catheter. The use of the stylet (98) is identical to that of the previously described stylets. Entry of the stylet into the catheter through the hole (96), of course, permits the stylet to be withdrawn from the catheter without requiring the catheter to be disconnected from the drainage tube (80).

The sheath (92) desirably extends rearwardly to or desirably beyond the rearward end of the catheter (86), and a small hole as shown in FIG. 13, in registration with the catheter hole (96), may be provided in the sheath to permit insertion of the stylet (98). When the stylet protrudes from the hole (96), rearward movement of the sheath (92) causes it desirably to rip along the tear line (94) as it contacts the stylet and provides a method of easily removing the sheath.

The tubular cover (82) carried by the drainage tube (80) similarly desirably extends beyond its upper or forward end, and preferably is joined to the sheath (92) along a part line of the type earlier described and designated (100) in FIG. 13. Either the sheath (92) or the tubular cover (82), or both, may have a portion which protectively encloses the connector means (90) which, as mentioned above, may include a plug, pump, or other apparatus. When the adjacent ends of the sheath (92) and tubular cover (82) are thus joined, they together provide a protective, generally sterile envelope that extends from the terminal end of the catheter to the terminal end of the drainage tube and which, as will now be described, provides a system enabling the catheter and drainage tube to be introduced into a patient with a minimum of exposure to infectious microorganisms. A lubricant may be provided between the confronting walls of the drainage tube (80) and protective tubular cover (82).

In use, the catheter portion of the shunt system is introduced into a ventricle in the manner described above. The sheath (92) is removed by drawing it rearwardly, and the stylet (98) is then withdrawn. To install the drainage tube, one may establish a subcutaneous "tunnel" leading from adjacent the burr hole in the scalp to the desired location in the body, e.g., the abdomen, through the use of a tunneling stylet of known design. The stylet may draw with it a suitable line of silk or other material. The trailing end of the line then is fastened to the end of the drainage tube (80). Referring to FIG. 14, (110) refers generally to tissue of the human body, with an incision in the overlying skin being designated (112). The line (114) is shown attached by means of a loop and knot to the lower end of the drainage tube (80). As the line (114) is drawn downwardly in the direction of the arrow, it pulls behind it the drainage tube (80), and the protective tubular cover (82) is collected at the wound opening (112), the cover tending to gather in accordian fashion. Once the drainage tube has been positioned as desired, the gathered tubular material (82) may be simply cut from the drainage tubing. Alternatively, the tubular covering material (82) may be provided, with a tear line shown at (115) in FIG. 13, and can be removed in the same manner as the sheath (92), as depicted in FIG. 14.

Use of the shunt system shown in FIGS. 13 and 14 maintains the interior of the catheter, connector and drainage tube in a substantially sterile condition since the connector means is not disconnected from the drainage tube or the catheter. The stylet (98), in sterile condition, is inserted in the catheter prior to insertion of the catheter itself into the brain tissue into a ventricle. Thus, there is substantially no access into the interior of the system for microorganisms found on the skin of a patient.

When catheters of the invention having flexible ventricular end portions are used, it is desirable to stiffen the catheters against lateral collapse and resulting blockage due to pressure exerted by walls of a ventricle. A helical wire of metal or other appropriate material may be embedded in the catheter walls to provide the desired stiffness, one such wire being shown at (35) in FIG. 4. It will be noted that helical wire reinforcements of this type remain axially extensible and will not unduly interfere with axial elongation of the ventricular catheter end portion resulting from insertion of a stylet, as described above.

Figure 15:
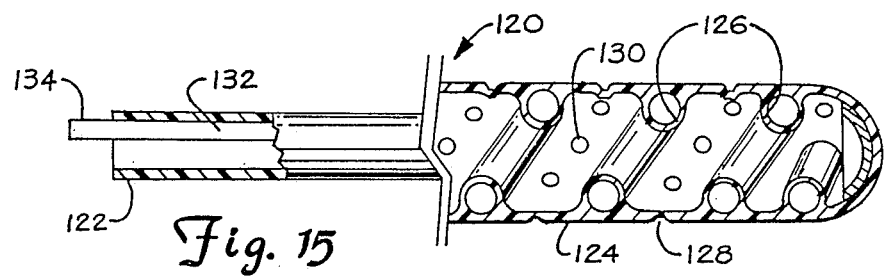
FIG. 15 is a broken-away view in partial cross-section of another embodiment of the invention.
Figure 16:
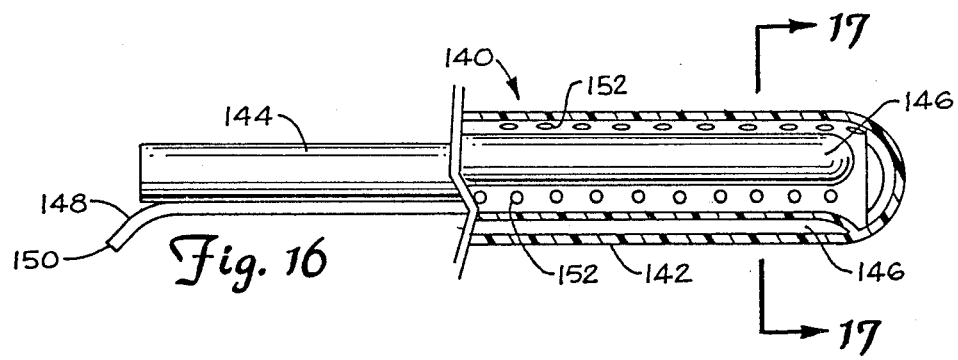
FIG. 16 is a broken-away view in partial cross-section of yet another embodiment of the invention.
Figure 17:
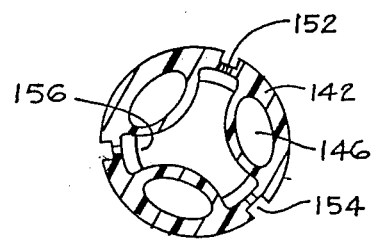
FIG. 17 is a cross-sectional view taken along line 17—17 of FIG. 16.

FIGS. 15–17 show alternate or additional means for laterally stiffening the ventricular catheter end portion against collapse. The catheter (120) shown in FIG. 15 is provided with a rearwardly extending portion (122) and a forward ventricular end portion (124) of increased diameter as previously shown in the embodiment depicted in FIG. 1. The walls of the ventricular end portion are provided with at least one elongated bladder (126) extending spirally or helically within the catheter between the helically positioned grooves (128) and drainage holes (130), the bladder being sealed at its forward end. A filler tube (132) extends within the catheter in fluid communication with the bladder (126), the tube extending rearwardly from the catheter and having an end (134) adapted to be connected to a syringe or other source of fluid under pressure. In use, the catheter (120) is to be inserted into a ventricle utilizing a stylet in the method described above in connection with the embodiment of FIG. 1. When the catheter has been properly placed, a fluid (a liquid or gas such as water or air) is injected into the tube (132) under pressure, the bladder becoming pressurized and hence relatively stiff to restrain lateral collapse of the catheter walls. The diameter of the elongated bladder when pressurized is desirably substantially less than the diameter of the catheter ventricular end portion; as a result, the diameter of the ventricular end portion remains substantially unchanged.

The embodiment of FIGS. 16 and 17 employs a catheter (140) having a forwardly extending ventricular end portion (142) and a rearward drainage portion (144). Elongated spaced bladders (146) having sealed forward ends (and desirably at least two in number) carried by the catheter wall extend parallel to the length of the catheter within the ventricular end portion (142). The bladders, which are desirably spaced equally about the circumference of the catheter, are connected to a filler tube (148) that extends rearwardly through the catheter and terminates in an end (150) attachable to a source of fluid under pressure. Drainage holes (152) are located between the bladders to receive cerebrospinal fluid, and if desired, the holes (152) may be positioned in exterior grooves (154) as shown in FIG. 17. The bladders (146), when pressurized with fluid, stiffen the ventricular end portion (142) of the catheter against collapse. Lateral pressure, as may be exerted by walls of a ventricle, may cause the bladders to come into contact with one another within the catheter but leave longitudinally extending spaces therebetween, as shown at (156) in FIG. 17, to facilitate continued drainage of cerebrospinal fluid.

It will be understood that the bladders depicted in the embodiments of FIGS. 15-17 are not highly pressurized; even when pressurized they will contain very little fluid and hence do not significantly affect the size of the catheters. The bladders, which are carefully manufactured to be leakfree, are desirably positioned internally of the catheters as shown in FIGS. 15-17. Pressure is maintained in the bladders by closing the interiors of the filler tubes as by pinching them shut with a clamp, bending and suturing, etc. When the catheter is to be removed, pressure is first released and a stylet is then inserted in accordance with the previously described procedure.

While a preferred embodiment of the present invention has been described, it should be understood that various changes, adaptations and modifications may be made therein without departing from the spirit of the invention and the scope of the appended claims.

What is claimed is:

1. A cerebrospinal fluid shunt system comprising a ventricular catheter, a flexible drainage tube for carrying cerebrospinal fluid from the catheter to a desired body location, connector means connecting the catheter and drainage tube and providing fluid communication therebetween, and flexible tubular cover means carried exteriorly of the drainage tube and from which the drainage tube can be drawn.

2. A cerebrospinal fluid shunt system including a ventricular catheter comprising a length of biologically acceptable tubing having a ventricular end portion adapted for insertion in the ventricle of a brain, the ventricular end portion of the catheter having an exterior surface provided with at least one helical groove formed therein and a closed tip, a plurality of holes formed through the wall of the catheter within the grooves, the ventricular end portion of the catheter being axially elastically extensible, stylet means insertable within the catheter and having an end adapted to contact and press against the tip of the catheter to cause the ventricular end portion thereof to extend elastically with resultant reduction in its diameter for facilitating insertion or removal of the catheter into or from a ventricle, a flexible protective sheath sheathing the catheter and including means enabling the sheath to be drawn rearwardly of the catheter to expose the ventricular end portion thereof, a drainage tube for carrying cerebrospinal fluid from the catheter to a desired body location, connector means connecting the catheter and drainage tube and providing fluid communication therebetween, and flexible tubular cover means carried exteriorly of the drainage tube and from which the drainage tube can be drawn.

3. The shunt system of claim 2 wherein the sheath and tubular cover have adjacent, joined ends providing a continuous sterile covering for the shunt system.

4. A ventricular catheter comprising a length of biologically acceptable tubing having a ventricular end portion adapted for insertion in the ventricle of a brain, the ventricular end portion having an exterior surface provided with at least one helical groove formed therein, and a closed tip, a plurality of holes formed through the walls of the catheter within the at least one groove, the ventricular end portion of the catheter being axially elastically extensible; and stylet means insertable within the catheter and having an end adapted to contact and press against the tip of the catheter to cause the ventricular end portion thereof to extend elastically with resultant reduction of its diameter, the diameter of the ventricular end portion being larger than that of the catheter portion contiguous thereto by an amount such that extension of the ventricular end portion of the catheter by stylet insertion is capable of reducing the diameter of the ventricular end portion to approximately that of the contiguous catheter portion.

5. A ventricular catheter having an end portion adapted to be received in a ventricle of the brain to drain cerebrospinal fluid therefrom, the end portion having walls provided with a plurality of drainage holes arranged in helically extending patterns to receive cerebrospinal fluid from the ventricle, the catheter including a flexible, protective sheath enclosing at least the end portion thereof and having holes adjacent its forward end in flow communication with drainage holes of the catheter to transmit cerebrospinal fluid to the catheter and to thus signal the onset of fluid flow from a ventricle, the sheath including an easily torn part line at the forward end thereof to enable it to be pulled rearwardly to open the part line and permit the sheath to be drawn rearwardly of the catheter to expose the catheter end.

6. A cerebrospinal fluid shunt system comprising a ventricular catheter having a forward ventricular end portion adapted for reception in a ventricle of the brain to drain cerebrospinal fluid therefrom, a flexible protective sheath enclosing at least the ventricular end portion of the catheter and having an easily parted forward end and including means enabling it to be drawn rearwardly of the catheter to expose the ventricular end portion thereof, a drainage tube for carrying cerebrospinal fluid from the catheter to a desired body location, connector means connecting the catheter and drainage tube and providing fluid communication therebetween, and flexible tubular cover means carried exteriorly of the drainage tube and from which the drainage tube can be drawn.

7. The shunt system of claim 6 wherein the sheath and tubular cover have adjacent, joined ends providing a continuous sterile covering for the shunt system.

8. A ventricular catheter having an end portion having a closed terminal end and adapted to be received in a ventricle of the brain to drain cerebrospinal fluid therefrom, the end portion having walls provided with a plurality of drainage holes arranged to define helically extending patterns to receive cerebrospinal fluid from a ventricle, stylet means insertable within the catheter and having an end adapted to contact and press against the tip of the catheter, and a flexible protective sheath enclosing at least the closed terminal end portion of the catheter and including an easily torn part line at its forward end, the sheath including means enabling it to be pulled rearwardly of the catheter as the latter is supported by the stylet to open the part line and permit the sheath to be drawn rearwardly of the catheter to expose the catheter end.

9. The catheter of claim 8 wherein said part line extends rearwardly along the length of the sheath to facilitate easy removal of the sheath from the catheter.

10. A ventricular catheter having an end portion having a closed terminal end and adapted to be received in a ventricle of the brain to drain cerebrospinal fluid therefrom, the end portion having walls provided with a plurality of drainage holes arranged to define helically extending patterns to receive cerebrospinal fluid from a ventricle, and a drainage tube for carrying cerebrospinal fluid from the catheter to a desired body location, connector means connecting the catheter and drainage tube and providing fluid communication therebetween, and flexible tubular cover means carried exteriorly of the drainage tube and from which the drainage tube can be drawn.

11. The shunt system of claim 10 including biocide means carried by the drainage tube for preventing the growth of harmful microorganisms therein.

12. A ventricular catheter having walls defining a longitudinally elastic ventricular end portion having a hollow interior and adapted to be received in a ventricle, the walls having spaced drainage holes therethrough to transmit cerebrospinal fluid from the ventricle to the hollow interior of the catheter when the ventricular end portion thereof is received in a ventricle, and bladder means comprising a plurality of elongated pressurizable bladders carried by the wall and positioned to stiffen the ventricular end portion, when pressurized, against lateral collapse without substantial increase in diameter of the ventricular end portion, said bladders being spaced apart in parallel relation to one another and positioned in unobstructing relationship to the drainage holes, the bladder means including means remote from the plurality of bladders for pressurizing and depressurizing the bladders.

13. A ventricular catheter having walls defining a longitudinally elastic ventricular end portion having a hollow interior and adapted to be received in a ventricle, the walls having spaced drainage holes therethrough arranged in one or more helical lines for receiving cerebrospinal fluid from the ventricle, and bladder means comprising at least one elongated pressurizable bladder carried by the wall and positioned to stiffen the ventricular end portion, when pressurized, against lateral collapse without substantial increase in diameter of the ventricular end portion and without occlusion of said drainage holes, the bladder being carried helically of the ventricular end portion between helical lines of the drainage holes, the bladder means including means remote from the at least one bladder for pressurizing and depressurizing the bladder.

* * * * *